S011440863B2" />

United States Patent
Kucmierczyk et al.

(10) Patent No.: US 11,440,863 B2
(45) Date of Patent: *Sep. 13, 2022

(54) PROCESS FOR PREPARING AN ALCOHOL FROM HYDROCARBONS

(71) Applicant: Evonik Operations GmbH, Essen (DE)

(72) Inventors: Peter Kucmierczyk, Herne (DE); Robert Franke, Marl (DE); Dirk Fridag, Haltern am See (DE); Johannes Knossalla, Schermbeck (DE); Marc Schäpertöns, Recklinghausen (DE); Frederik Gluth, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 150 days.

This patent is subject to a terminal disclaimer.

(21) Appl. No.: 16/888,920

(22) Filed: Jun. 1, 2020

(65) Prior Publication Data

US 2020/0392057 A1 Dec. 17, 2020

(30) Foreign Application Priority Data

Jun. 12, 2019 (EP) .................................... 19179572

(51) Int. Cl.
| | | |
|---|---|---|
| *C07C 29/149* | (2006.01) | |
| *C07C 67/38* | (2006.01) | |
| *C07C 29/76* | (2006.01) | |
| *C07C 29/78* | (2006.01) | |
| *C07C 29/80* | (2006.01) | |
| *C07C 29/86* | (2006.01) | |
| *B01J 31/22* | (2006.01) | |
| *C07C 67/48* | (2006.01) | |
| *C07C 29/132* | (2006.01) | |
| *C07C 67/03* | (2006.01) | |

(52) U.S. Cl.
CPC ......... *C07C 29/149* (2013.01); *B01J 31/2234* (2013.01); *C07C 29/132* (2013.01); *C07C 29/76* (2013.01); *C07C 29/78* (2013.01); *C07C 29/80* (2013.01); *C07C 29/86* (2013.01); *C07C 67/38* (2013.01); *C07C 67/48* (2013.01); *B01J 2523/824* (2013.01); *B01J 2531/004* (2013.01); *C07C 67/03* (2013.01)

(58) Field of Classification Search
None
See application file for complete search history.

(56) References Cited

U.S. PATENT DOCUMENTS

| | | | |
|---|---|---|---|
| 6,140,545 A | 10/2000 | Merger et al. | |
| 9,676,805 B2 | 6/2017 | Dyballa et al. | |
| 9,688,604 B2 | 6/2017 | Jennerjahn et al. | |
| 9,725,398 B2 | 8/2017 | Dong et al. | |
| 9,845,276 B2 | 12/2017 | Franke et al. | |
| 10,077,228 B2 | 9/2018 | Dong et al. | |
| 10,155,200 B2 | 12/2018 | Geilen et al. | |
| 10,202,329 B2 | 2/2019 | Dong et al. | |
| 10,245,578 B2 | 4/2019 | Klasovsky et al. | |
| 10,294,191 B2 | 5/2019 | Dong et al. | |
| 10,501,392 B2 | 12/2019 | Fridag et al. | |
| 10,562,833 B2 | 2/2020 | Fridag et al. | |
| 10,562,838 B2 | 2/2020 | Fang et al. | |
| 10,577,297 B2 | 3/2020 | Fridag et al. | |
| 10,633,302 B2 | 4/2020 | Nadolny et al. | |
| 10,647,650 B2 | 5/2020 | Hecht et al. | |
| 10,654,784 B2 | 5/2020 | Hasselberg et al. | |
| 2009/0012323 A1 | 1/2009 | Van Rensburg et al. | |
| 2016/0236150 A1* | 8/2016 | Geilen ................... B01J 31/185 |
| 2016/0257634 A1 | 9/2016 | Dyballa et al. | |
| 2017/0007963 A1* | 1/2017 | Livingston ............. B01D 71/52 |
| 2017/0022138 A1 | 1/2017 | Dong et al. | |
| 2019/0283003 A1 | 9/2019 | Nadolny et al. | |
| 2019/0283004 A1 | 9/2019 | Nadolny et al. | |
| 2019/0283005 A1 | 9/2019 | Nadolny et al. | |

FOREIGN PATENT DOCUMENTS

| | | | |
|---|---|---|---|
| CA | 2311589 A1 | 6/1999 | |
| CN | 106748644 A * | 5/2017 | |
| EP | 0 937 698 A1 | 8/1999 | |
| EP | 1 042 260 A1 | 10/2000 | |
| EP | 1 338 557 A1 | 8/2003 | |
| EP | 3 121 184 A2 | 1/2017 | |
| EP | 3 272 733 A1 | 1/2018 | |
| GB | 2 529 007 A | 2/2016 | |
| WO | 99/31035 A1 | 6/1999 | |
| WO | 2012/074841 A2 | 6/2012 | |
| WO | WO-2013107902 A1 * | 7/2013 | ............. B01D 61/58 |
| WO | 2015/110843 A1 | 7/2015 | |

OTHER PUBLICATIONS

CN106748644A, translation, May 2017, pp. 1-16 (Year: 2017).*
European Search Report dated Dec. 3, 2019 in EP 19179572.3 (8 pages).
Kucmierczyk et al., U.S. Appl. No. 16/893,463, filed Jun. 5, 2020.
Kucmierczyk et al., U.S. Appl. No. 16/893,481, filed Jun. 5, 2020.
Kucmierczyk et al., U.S. Appl. No. 16/888,925, filed Jun. 1, 2020.

* cited by examiner

*Primary Examiner* — Medhanit W Bahta
(74) *Attorney, Agent, or Firm* — Taylor English Duma LLP; Philip P. McCann

(57) ABSTRACT

The invention provides a process for preparing an alcohol by hydrogenating an ester which is obtained by alkoxycarbonylating a C2 to C20 hydrocarbon having at least one multiple bond, preferably having at least one olefinic double bond, in which the homogeneous catalyst system used is separated from the product mixture by means of membrane separation. In a development of the present invention, the ester thus formed is converted to another ester by transesterification and then hydrogenated.

16 Claims, No Drawings

PROCESS FOR PREPARING AN ALCOHOL FROM HYDROCARBONS

CROSS REFERENCE TO RELATED APPLICATIONS

This application is a 35 U.S.C. § 119 patent application which claims the benefit of European Application No. 19179572.3 filed Jun. 12, 2019, which is incorporated herein by reference in its entirety.

FIELD

The present invention relates to a process for preparing an alcohol by hydrogenating an ester which is obtained by alkoxycarbonylating a C2 to C16 hydrocarbon having at least one multiple bond, preferably having at least one olefinic double bond, in which the homogeneous catalyst system used is separated from the liquid product mixture by means of membrane separation. In a development of the present invention, the ester thus formed is converted to another ester by transesterification and then hydrogenated.

BACKGROUND

The production of alcohols in large-scale industrial chemistry is achieved largely by hydroformylation to produce an aldehyde, with subsequent hydrogenation of the aldehyde to the alcohol. Although the production of alcohols through hydroformylation with subsequent hydrogenation has been an industrially established and proven process for decades, there is still potential for improvement. One problem with this synthesis route is that pressures and temperatures in the hydroformylation are usually high, and hence comparatively high technical demands are made on the plants used. Ultimately, the plants have to be able to withstand the pressures and temperatures.

Another fundamental problem in the production of alcohols by hydroformylation and subsequent hydrogenation is the high reactivity of the aldehydes formed as intermediates. The aldehydes are very reactive and carry on reacting to form unwanted by-products before the desired hydrogenation can take place. These unwanted by-products are mostly high-boiling substances that must be laboriously separated from the reaction mixture and disposed of. Moreover, the formation of high boilers invariably means losses of aldehydes that can no longer be converted to the desired alcohols. This brings down the selectivity of the overall process.

It was therefore an object of the present invention to provide an alternative synthesis route for the preparation of alcohols in which lower apparatus complexity is required in the carbonylation. A further important objective is that the manufacturing process can be carried out on a large industrial scale. Central to this is the replacement of the classic synthesis by a different synthesis technology that provides the products of classic hydroformylation in better quality. In addition, the new synthesis route to be established should give rise to a lower level of unwanted by-products.

US 2009/012323 A1 describes a comparable synthesis method. But the problem here is that a distillation is conducted immediately subsequent to the preparation of the ester, in order to separate the ester from the product mixture. It is apparent that the catalyst-containing product mixture here is subjected to the distillation. However, the result of such a thermal treatment can be that the catalyst is deactivated or even separates out and hence is no longer available. Specifically in the case of the transition metals typically used, this is associated with high costs since those that are removed from the reactor have to be replaced. Another underlying object was therefore that of improving known processes by reduction of complexity and costs.

SUMMARY

This object is achieved by a two-stage process in which, in a first step, a hydrocarbon having at least one multiple bond undergoes an alkoxycarbonylation reaction with carbon monoxide and an alcohol to form an ester, and in which, in a second step, the ester undergoes a hydrogenation reaction with hydrogen to form the desired target alcohol. In the second step of this process, some of the alcohol originally used is released again.

DETAILED DESCRIPTION

According to the invention, the process for preparing a target alcohol comprises the following steps:

a) preparing an ester by reacting (carbonylating) a C2 to C16 hydrocarbon having at least one multiple bond with carbon monoxide and with an alcohol A which is a mono- or polyalcohol (two or more OH groups) having 1 to 50 carbon atoms or is a mixture of two or more mono- and/or polyalcohols and which is used in a molar ratio to the C2 to C16 hydrocarbon (alcohol:C2 to C16 hydrocarbon) of 2 to 20, in the presence of a homogeneous catalyst system comprising at least one metal of groups 8 to 10 of the Periodic Table of the Elements or a compound thereof, a phosphorus-containing ligand and an acid, in a reaction zone to obtain a liquid product mixture;

b) performing a membrane separation to separate the homogeneous catalyst system from the liquid product mixture, which enriches the homogeneous catalyst system and additionally unconverted hydrocarbon and/or unconverted alcohol A in the retentate and enriches the ester formed in step a) in the permeate, wherein the membrane material used is an OSN (organic solvent nanofiltration) membrane material which is acid-stable, i.e. stable in the presence of the acid of the catalyst system for at least 300 h, and which has at least one separation-active layer, and wherein the retentate is returned to the reaction zone in step a) and the permeate is routed to the subsequent step c);

c) separating the ester formed in step a) from the permeate in at least one separation process step selected from thermal separation, for example distillation, extraction, crystallization and membrane separation;

d) hydrogenating the ester separated in step c) with hydrogen in the presence of the heterogeneous catalyst system in a hydrogenation zone to obtain an alcohol mixture comprising at least the target alcohol, the eliminated alcohol A and unconverted esters;

e) separating the target alcohol formed in step d) in at least one separation process step selected from thermal separation, for example distillation, extraction, crystallization and membrane separation.

The hydrocarbons used in the reaction in step a) must have at least one multiple bond. Preference is given to hydrocarbons having at least one olefinic double bond and particular preference to hydrocarbons having one olefinic double bond. There is in principle no limit to the number of carbon atoms in the compound having at least one multiple bond, preferably at least one olefinic double bond. However, only the carbonylation of C2 to C20 hydrocarbons having at least one multiple bond, preferably at least one olefinic double bond, is industrially relevant. In a preferred embodiment of the present invention, C3 to C16 hydrocarbons, more preferably C4 to C12 hydrocarbons, having at least one multiple bond, preferably at least one olefinic double bond, may be used. These include in particular n-alkenes, isoalkenes, cycloalkenes and aromatic alkenes having 2 to 20 carbon atoms, preferably 3 to 16 carbon atoms, more preferably 4 to 12 carbon atoms.

The hydrocarbons described above may contain one or more further functional groups in addition to the at least one olefinic double bond. Examples of suitable functional groups are carboxyl, thiocarboxyl, sulfo, sulfinyl, carboxylic anhydride, imide, carboxylic ester, sulfonic ester, carbamoyl, sulfamoyl, cyano, carbonyl, carbonothioyl, hydroxyl, sulfhydryl, amino, ether, thioether, aryl, heteroaryl or silyl groups and/or halogen substituents.

Particularly preferred hydrocarbons used in step a) of the process according to the invention have only one olefinic double bond, in particular n-alkenes and isoalkenes having 2 to 20 carbon atoms, preferably 3 to 16 carbon atoms, more preferably 4 to 12 carbon atoms. The hydrocarbons used are preferably unsubstituted.

The employed and above-described hydrocarbons having an olefinic double bond are according to the invention reacted in step a) with carbon monoxide (CO) and an alcohol to form the corresponding ester. The carbon monoxide may be provided directly as a feed mixture or by adding a carbon monoxide-containing gas selected from synthesis gas, water gas, generator gas and other carbon monoxide-containing gases. It is also possible to provide the carbon monoxide by first separating the carbon monoxide-containing gas into its components in a manner known to those skilled in the art and passing the carbon monoxide into the reaction zone. The carbon monoxide may still contain a certain proportion of hydrogen or other gases, because complete separation is almost impossible.

The alcohol used in the reaction in step a) is a mono- or polyalcohol (two or more OH groups) having 1 to 50 carbon atoms, preferably 1 to 15 carbon atoms, more preferably 1 to 10 carbon atoms, or a mixture of two or more mono- and/or polyalcohols. In a preferred embodiment, the polyalcohol is a diol, triol or tetraol, preferably a diol or triol, having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol or mixtures thereof.

The alcohol used in step a), when it is a monoalcohol, is used in a molar ratio to the hydrocarbon used (monoalcohol:hydrocarbon) of 2 to 20, preferably of 3 to 10 and more preferably of 4 to 6. The monoalcohol is thus added in a molar excess—based on the hydrocarbon used. The alcohol may accordingly serve both as a reactant for the carbonylation and as solvent. The alcohol used in step a), when it is a polyalcohol, is used in a molar ratio to the hydrocarbon used (hydrocarbon:polyalcohol) of 2 to 20, preferably of 3 to 10 and more preferably of 4 to 8. The polyalcohol is thus added in a molar deficiency based on the hydrocarbon used.

The reaction according to the invention in step a) is carried out in the presence of a homogeneous catalyst system. The homogeneous catalyst system preferably comprises at least one metal from groups 8 to 10 of the Periodic Table of the Elements (PTE) or a compound thereof, a phosphorus-containing ligand and an acid as co-catalyst.

The metal from groups 8 to 10 of the PTE is preferably palladium. The palladium is preferably used in the form of a precursor compound as a palladium compound coordinated by the phosphorus-containing ligand. Examples of palladium compounds that may be used as precursor compounds are palladium chloride [$PdCl_2$], palladium(II) acetylacetonate [$Pd(acac)_2$], palladium(II) acetate [$Pd(OAc)_2$], dichloro(1,5-cyclooctadiene)palladium(II) [$Pd(cod)_2Cl_2$], bis(dibenzylideneacetone)palladium(0) [$Pd(dba)_2$], tris(dibenzylideneacetone)dipalladium(0) [$Pd_2(dba)_3$], bis(acetonitrile)dichloropalladium(II) [$Pd(CH_3CN)_2Cl_2$], palladium(cinnamyl)dichloride [$Pd(cinnamyl)Cl_2$]. Preference is given to using the compounds [$Pd(acac)_2$] or [$Pd(OAc)_2$]. The concentration of palladium metal in step a) is preferably between 0.01 and 0.6 mol %, preferably between 0.03 and 0.3 mol %, more preferably between 0.04 and 0.2 mol %, based on the molar amount of the hydrocarbon used.

Suitable phosphorus-containing ligands of the catalyst system according to the invention preferably have a bidentate structure. Preferred phosphorus-containing ligands for the catalyst system according to the invention are benzene-based diphosphine compounds, as disclosed, for example, in EP 3 121 184 A2. The ligands may be combined with the palladium in a preliminary reaction so that the palladium-ligand complex is fed into the reaction zone or added to the reaction in situ and combined with the palladium there. The molar ratio of ligand to metal for the reaction described in step a) may be 1:1 to 10:1, preferably 2:1 to 6:1, more preferably 3:1 to 5:1.

The homogeneous catalyst system further comprises an acid, in particular a Brønsted or a Lewis acid. Lewis acids used may especially be Lewis acids having an LAU value of more than 25, preferably having an LAU value of 29. The LAU value is a new method of determining the strength of Lewis acids (J R Gaffen et al., Chem, Vol. 5, Issue 6, p. 1567-1583). Lewis acids used are preferably aluminium triflate, aluminium chloride, aluminium hydride, trimethylaluminium, tris(pentafluorophenyl)borane, boron trifluoride, boron trichloride or mixtures thereof. Of the Lewis acids mentioned, preference is given to using aluminium triflate. The Lewis acid is preferably added in a molar ratio of Lewis acid to ligand of 1:1 to 20:1, preferably 2:1 to 15:1, more preferably 5:1 to 10:1.

Suitable Brønsted acids preferably have an acid strength pKa of ≤5, more preferably an acid strength pKa of ≤3. The stated acid strength pKa refers to the pKa determined under standard conditions (25° C., 1.01325 bar). For a polyprotic acid, the acid strength pKa in the context of this invention relates to the pKa of the first protolysis step. The Brønsted acid is preferably added in a molar ratio of Brønsted acid to ligand of 1:1 to 15:1, preferably 2:1 to 10:1, more preferably 3:1 to 5:1.

The Brønsted acids used may in particular be perchloric acid, sulfuric acid, phosphoric acid, methylphosphonic acid or sulfonic acids. Examples of suitable sulfonic acids are methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid and dodecylsulfonic acid. Particularly preferred acids are sulfuric acid, methanesulfonic acid, trifluoromethanesulfonic acid and p-toluenesulfonic acid. The acid is preferably sulfuric acid.

The reaction/carbonylation in step a) of the employed hydrocarbon having an olefinic double bond is preferably carried out at a temperature of 25 to 140° C., more preferably at a temperature of 80 to 130° C. and particularly preferably at a temperature of 90 to 120° C. The pressure in step a) may be 5 to 60 bar, preferably 10 to 40 bar, more preferably 15 to 30 bar.

The described reaction in step a) takes place in a suitable reaction zone. The reaction zone for the reaction comprises at least one reactor, but may also consist of two or more reactors. The at least one reactor may in particular be selected from the group consisting of a stirred-tank reactor, a loop reactor, a jet-loop reactor, a bubble-column reactor or combinations thereof. If more than one reactor is used, the reactors may be identical or different.

The above-described reaction in step a) affords a liquid product mixture comprising at least the ester formed by the reaction, the homogeneous catalyst system, unconverted alcohols A, and possibly further components such as low boilers, for example low-boiling by-products such as ethers, and/or high boilers and/or unconverted hydrocarbons. The liquid product mixture is then fed to the subsequent membrane separation in step b). In the reaction in step a), an offgas that consists at least of unreactive impurities such as nitrogen, hydrogen and low-boiling by-products (for example the ethers already mentioned) may also be removed from the reaction zone. The impurities and low-boiling by-products could accumulate and, over time, lower the partial pressure of the reaction gas (CO), thereby slowing down the reaction.

In step b) that follows, the liquid product mixture is fed to a membrane separation to separate the homogeneous catalyst system from the liquid product mixture. The membrane material according to the invention causes enrichment of the homogeneous catalyst system and unconverted hydrocarbon and/or unconverted alcohol in the retentate, whereas the ester formed in step a) is enriched in the permeate. The permeate containing the ester formed is then conducted to the subsequent step c). The retentate comprising the enriched homogeneous catalyst system is then recycled into the reaction zone in step a). On recycling the retentate, a purge stream that may contain inert alkanes, low-boiling by-products (for example ethers), possible decomposition products of the catalyst system or other impurities introduced by the hydrocarbon streams used, for example traces of water or nitrogen, may additionally be removed to avoid accumulation in the reaction zone(s). The recycling of the retentate ensures that the catalyst system obtained in the retentate in the membrane separation is returned to the reaction. This minimizes catalyst losses through deposition or deactivation (occurring in the case of distillations, for example), and makes the process less costly. Catalyst losses usually cannot be avoided entirely, but the effect of the decrease in the losses mentioned is that less catalyst has to be replaced by supply of fresh catalyst.

Membrane separation is based on the semipermeability of the membrane material, which is permeable to certain substances and impermeable to others. The membrane material used in step b) of the process according to the invention is an OSN membrane material (OSN=organic solvent nanofiltration). Such a membrane material preferably consists at least of a relatively thin active separation-active layer (also: active separation layer) and optionally a thicker backing on which the separation-active layer is located. The membrane material according to the invention preferably consists at least of a separation-active layer and a backing. One or more intermediate layers may be present between the separation-active layer and the backing. In a preferred embodiment, the membrane material consists solely of the separation-active layer and the backing. The membrane material, composed at least of separation-active layer and backing, should be acid-stable so that the membrane material is not damaged by the acid present as co-catalyst in the liquid product mixture. What is meant by the term "acid-stable" in the context of the present invention is that the membrane material is stable and is not destroyed in the presence of the acid in the catalyst system for at least 300 h, especially a Brønsted acid having a $pKa \leq 5$, more preferably having a $pKa \leq 3$, or a Lewis acid having an LAU value of more than 25, preferably having an LAU value of 29, as a result of which the actual separating action could no longer be achieved.

In particular, the backing has a porous structure that is permeable to the permeate that has passed through the separation-active layer. The backing has a stabilizing function and serves as a support for the separation-active layer. The backing may in principle be composed of any suitable porous material. A prerequisite, however, is that the material is stable to acids and bases. The backing may also consist of the same material as the separation-active layer.

The separation-active layer according to the invention is preferably composed of a PAEK (polyaryl ether ketone) polymer. PAEK has the particular feature that, within the repeat unit, aryl groups are linked alternately via an ether functionality and a ketone functionality. A separation-active layer which is preferred according to the invention is composed of PEEK (polyether ether ketone). As the separation-active layer, particular preference is given to using PEEK polymers having a degree of sulfonation of less than 20%, particularly preferably having a degree of sulfonation of less than 10%. The corresponding PEEK polymers and the preparation thereof are described in WO 2015/110843 A1 or in J. da Silva Burgal et al.; Journal of Membrane Science, vol. 479 (2015), pp. 105-116. This material has surprisingly been found to be particularly stable, particularly also towards the acid as co-catalyst of the homogeneous catalyst system. In addition, a particular feature of the PEEK material according to the invention is that, when used as a separation-active layer, it allows the esters that are formed to pass through preferentially, whereas even the alcohols used as reactants are at least partially retained and thereby accumulate in the retentate. This allows the subsequent processing of the residual liquid product mixture to be carried out more economically and for longer, because fewer alcohols need to be removed compared with known membrane materials.

The membrane separation in step b) is carried out preferably at a temperature of 25 to 100° C., more preferably 30 to 80° C. and particularly preferably 40 to 70° C. In order to bring the liquid product mixture to the prevailing temperature preferred for the membrane separation, the product mixture may be cooled. In addition to active cooling using a coolant, cooling may also be achieved via a heat exchanger, whereby another stream is heated within the process according to the invention. Optionally, there is also a degassing step between the reaction zone in step a) and the membrane separation in step b), in order to remove volatile compounds such as carbon monoxide and/or residual unreactive impurities that have not been removed via the offgas, such as nitrogen, hydrogen, alkanes and low-boiling by-products (for example the ethers already mentioned) from the liquid product mixture beforehand. The product mixture is first depressurized below the partial pressure of the dissolved components, such as carbon monoxide, so that they are displaced from solution, thereby allowing the pressure to then be raised again as specified for the membrane separation.

The transmembrane pressure (TMP) in step b) may be 10 to 60 bar, preferably 15 to 55 bar, more preferably 20 to 50 bar (relative). The permeate-side pressure may here be above atmospheric pressure up to 15 bar, preferably 3 to 7 bar, which then gives rise to the retentate-side pressure brought about by the TMP. In a preferred embodiment, care should be taken, in the case of the pressure ratios and the permeate-side pressure in particular, to ensure that the pressure is set according to the hydrocarbon used, the alcohol used and the temperature in the system, in order to avoid evaporation after passage through the membrane, since this could make the entire operation unstable. The same applies in principle also to dissolved components such as carbon monoxide, which may optionally be removed by the degassing step already mentioned.

The economics of membrane separation processes can be substantially determined by the service life of the membrane materials used, which is why the service life/stability of the membrane can likewise be a criterion for selecting the suitable membrane material. A minimum service life of about half a year is assumed. This can be particularly relevant for processes, such as the present process, in which the product is enriched in the permeate, because the membrane surface area needed increases with the total capacity of the process.

In the subsequent step c), to separate the ester formed in step a) from the remaining permeate, the permeate from the membrane separation (step b)) is subjected to a separation process selected from the group consisting of a thermal separation, for example distillation, an extraction, a crystallization or a further membrane separation. The separation process is preferably a distillation. The appropriate process conditions are known to those skilled in the art.

In the separation process used in step c) and in the distillation in particular, there is the possibility that this separates from the permeate not just the ester that is formed, but the high boilers that have possibly formed too, for example high-boiling by-products that can arise in the reaction in step a). In order to remove these high boilers, the process according to the invention may include a purification step, i.e. a step in which the ester formed is purified by separating the ester from high boilers present in the permeate by means of thermal separation, extraction, crystallization or membrane separation. The esters formed are preferably purified using a thermal separation process, more preferably a further distillation. The process conditions are known to those skilled in the art.

In a preferred embodiment, the permeate obtained in step c), which is largely freed of the ester formed in step a) and comprises at least unconverted alcohols and/or unconverted hydrocarbons, undergoes a separation of recyclable components. In this separation, the unconverted alcohols and/or unconverted hydrocarbons are separated from the remaining permeate, in particular from the low boilers contained therein, by means of thermal separation, extraction, crystallization or membrane separation. The unconverted alcohols and/or unconverted hydrocarbons are separated from the remaining permeate preferably by means of a thermal separation process, more preferably a further distillation. The process conditions are known to those skilled in the art. The unconverted alcohols and/or unconverted hydrocarbons obtained here may then be recycled into the reaction zone.

The ester formed by the process according to the invention may be transesterified in two further process steps c1) and c2). In this transesterification, the part of the ester that corresponds to the first alcohol A used in step a) is replaced by a second alcohol B. This transesterification is carried out after step c) mentioned above, optionally after the possible purification step, and comprises the following steps:

c1) transesterifying the ester formed in step a) with a second alcohol B, where this second alcohol B differs from the alcohol A used in step a), in a second reaction zone to obtain a second liquid product mixture comprising at least the ester with the second alcohol B, the eliminated first alcohol A and unconverted second alcohols B;

c2) separating the ester formed with the second alcohol B from the rest of the second liquid product mixture and especially from the eliminated first alcohol A by thermal separation and/or by means of membrane separation, and recycling the eliminated first alcohol A into the reaction zone from step a) and also recycling the unconverted alcohol B into the second reaction zone.

Step c1) is where the actual transesterification takes place, that is to say the elimination of the first alcohol A actually attached in step a) and the attachment of the second alcohol B. In this step, the ester formed in step a) is reacted in a reaction zone with a second alcohol B that differs from the first alcohol A. In a particularly preferred embodiment, the second alcohol B used in the transesterification is a higher-boiling alcohol compared with the first alcohol A used in step a). In order to favor the transesterification reaction, the second alcohol B is preferably added in excess in the transesterification.

The second alcohol used in the transesterification in step c1) is preferably a mono- or polyalcohol (more than 2 OH groups) having 1 to 50 carbon atoms, more preferably having 1 to 15 carbon atoms, particularly preferably having 1 to 10 carbon atoms, or a mixture of two or more mono- and/or polyalcohols, with the proviso that the first alcohol A used in step a) and the second alcohol B are non-identical. In a preferred embodiment, the polyalcohol is a diol, triol or tetraol, preferably a diol or triol, having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol, pentaerythritol, neopentyl glycol, trimethylolpropane, dipentaerythritol or mixtures thereof, preferably ethanol, 1-propanol, 1-butanol, 1-pentanol, 1-hexanol, 2-propanol, tert-butanol, 3-pentanol, 2-propylheptanol.

The transesterification in step c1) is preferably carried out under acid or base catalysis. The acids used may be Brønsted or Lewis acids.

Suitable Brønsted acids for the transesterification in step c1) are perchloric acid, sulfuric acid, phosphoric acid, methylphosphonic acid or a sulfonic acid, for example methanesulfonic acid, trifluoromethanesulfonic acid, tert-butanesulfonic acid, p-toluenesulfonic acid (pTSA), 2-hydroxypropane-2-sulfonic acid, 2,4,6-trimethylbenzenesulfonic acid or dodecylsulfonic acid. The Brønsted acid used is preferably sulfuric acid or a sulfonic acid, more preferably sulfuric acid. Metal or compounds thereof may also be used, for example tin powder, tin(II) oxide, tin(II) oxalate, titanic esters such as tetraisopropyl orthotitanate or tetrabutyl orthotitanate and also zirconium esters such as tetrabutyl zirconate and also sodium methoxide and potassium methoxide.

Suitable Lewis acids for the transesterification in step c1) are titanium(IV) isopropoxide, $Bu_2SnO$, $BuSn(O)OH$ or aluminium triflate. Preference is given to using titanium(IV) isopropoxide and aluminium triflate as Lewis acids.

Suitable bases for the transesterification in step c1) are alkali metals, alkali metal alkoxides, alkali metal or alkaline earth metal acetates or oxides, alkali metal or alkaline earth metal alkoxides such as NaEtOH or MgEtOH, or alkali metal carbonates such as $K_2CO_3$ or $Cs_2CO_3$. Basic ion exchangers or NaOH may, however, also be used. Preference is given to using Na or Mg alkoxides such as NaEtOH or MgEtOH.

The acid-catalyzed transesterification is preferably carried out at a temperature from 60 to 220° C., more preferably from 100 to 210° C. and particularly preferably at 130 to 200° C. The reaction preferably takes place above the boiling point of the first alcohol A to be eliminated so as to remove the eliminated first alcohol A directly from the reaction mixture and thus promote a shift in equilibrium to the product side. The second alcohol B is preferably added to the ester formed in step a) in a significant excess, for example 30:1.

The base-catalyzed transesterification takes place preferably at a temperature of 20 to 100° C.

The described transesterification affords a second liquid product mixture comprising at least the ester with the second alcohol B, the eliminated first alcohol A and unconverted second alcohols B.

The second ester formed in step c1) is separated from the remaining second liquid product mixture in the subsequent step c2). The separation is carried out by means of thermal separation, preferably distillation, and/or by means of membrane separation, in particular using the membrane materials described above. The appropriate process conditions are known to those skilled in the art.

In the separation process used in step c2) and in the distillation in particular, there is the possibility that this separates from the rest of the second liquid product mixture not just the ester formed, but high boilers that have possibly formed too, for example high-boiling by-products that can arise in the reaction in step c1). In order to remove these high boilers, the process according to the invention may include a purification step, i.e. a step in which the ester formed in step c1) is purified by separating the ester from the high boilers present by means of thermal separation, extraction, crystallization or membrane separation. The esters formed are preferably purified using a thermal separation process, more preferably a further distillation. The process conditions are known to those skilled in the art.

The ester prepared in step a) and separated from the permeate in step c) and optionally purified then undergoes a hydrogenation in step d). The ester group is cleaved by the hydrogen used in this process, resulting in the formation of the target alcohol and allowing the alcohol A bound in the ester formation in step a) or the alcohol B bound in the transesterification to be recovered. The hydrogenation accordingly gives rise to an alcohol mixture that comprises at least the target alcohol, alcohol A or B and unconverted esters.

Without transesterification, the alcohol A recovered with the hydrogenation in step d) can be separated from the resulting alcohol mixture in a subsequent process step and recycled into the first reaction zone. If a transesterification has been carried out with recovery of the alcohol B in the hydrogenation in step d), this subsequent process step can be separated from the alcohol mixture formed and recycled into the second reaction zone.

The typical hydrogenation conditions are known to those skilled in the art and are disclosed, for example, in EP 1 042 260 A1. The hydrogenation according to the invention in step d) is preferably carried out at a pressure of 10 to 300 bar, more preferably at a pressure of 100 to 280 bar and particularly preferably at a pressure of 150 to 270 bar. The hydrogenation temperature is preferably between 100° C. and 300° C., preferably between 150° C. and 280° C. and particularly preferably between 180° C. and 220° C. During the hydrogenation, an offgas can additionally be withdrawn to remove low-boiling components, for example impurities such as nitrogen or low-boiling by-products.

The hydrogenation in step d) takes place in the presence of a heterogeneous catalyst system. Typical catalyst systems are known for example from EP 1 338 557 A1. The heterogeneous catalyst system preferably comprises a metal from the group consisting of copper, rhodium, ruthenium, rhenium or compounds of these metals. In addition, catalyst systems based on copper-chromium oxide are also suitable. Particularly preferred catalyst systems contain copper and/or zinc as the active component, which are applied to a support material. Porous silica and/or alumina are suitable as the support material.

The hydrogen required for the hydrogenation may be supplied directly as feedstock. It is also possible to supply the hydrogen by separating a hydrogen-containing gas beforehand into its components in a manner known to those skilled in the art and conveying the hydrogen to the hydrogenation zone. The hydrogen may still contain a certain proportion of carbon monoxide or other gases, because complete separation is almost impossible.

In the subsequent step e), to separate the target alcohol formed in step d) from the rest of the alcohol mixture, the alcohol mixture from the hydrogenation in step d) is subjected to at least one separation process step selected from the group consisting of a thermal separation, for example distillation, an extraction, a crystallization or a further membrane separation. The separation process is preferably a distillation. The appropriate process conditions are known to those skilled in the art. It is also possible to perform a multistage distillation.

In the at least one separation process step, the alcohols A and B used may additionally also be removed and recycled into the first or second reaction zone respectively. During recycling, a purge stream may be withdrawn in order for example to discharge hydrogenation by-products such as inert alkanes, aldehydes, acetals, ethers, ketones or carbons from the process.

For characterization of the permeability or separation performance of a membrane in membrane technology, the retention R of the membrane in respect of a specific component of the substance mixture is defined according to the following formula (1):

$$R = 1 - w_{(i)P}/w_{(i)R} \quad (1)$$

where $w_{(i)P}$ is the mass fraction of the relevant component in the permeate and $w_{(i)R}$ is the mass fraction of the relevant component in the membrane retentate. The retention may thus have a value from 0 to 1 and is therefore preferentially stated in %. A retention of 0% means that the relevant component permeates unhindered through the membrane, with the result that the mass fractions of the components in the retentate are the same as in the permeate. Conversely, a retention of 100% means that the relevant component is retained completely by the membrane, but this is almost impossible industrially.

In addition to the retention, the so-called permeability of the membrane is also key to the characterization of its permeability according to the following formula (2):

$$P = m'/(A*\text{TMP}) \quad (2)$$

where m' represents the mass flow rate of the permeate, A the surface area of the membrane and TMP the applied transmembrane pressure. The permeability is usually stated in units of $kg/(h*m^2*bar)$. Permeability is thus a characteristic normalized to the membrane area and the TMP established.

As regards characterization of the stability of a membrane, a relative change in the permeability $P_{Rel}$ can be defined according to the following formula (3):

$$P_{Rel} = P_{t=x}/P_{t=0} \quad (3)$$

where $P_{t=x}$ represents the permeability at time $t=x$ and $P_{t=0}$ the original permeability at time $t=0$ (a different reference time is also possible, with the proviso that $t=x>t=y$).

Example 1

Conversion of Diisobutene (DiB) to Methyl 3,5,5-trimethylhexanoate (TMH Ester) with Membrane Separation as Catalyst Recycling DiB is a mixture consisting of the two C8 isomers 2,4,4-trimethylpent-1-ene and 2,4,4-trimethylpent-2-ene in ratios of about 80:20. The experiments were conducted in a continuously operated pilot plant with the setup that follows.

The plant basically consists of a 200 ml glass autoclave (=reactor) from Büchi (pressure-rated up to 10 bar). The autoclave is fed from a glass reservoir filled with reaction solution and blanketed with argon by means of Knauer HPLC pumps. A further Knauer HPLC pump pumps from the glass autoclave into the separate high-pressure circuit which is pressure-rated up to 60 bar. The high-pressure circuit of the pilot plant consists essentially of a liquid circuit which is operated by means of a circulation pump, and a flat membrane test cell, and also the required sensors (e.g. pressure measurement, measurement of temperature). Circulation in the high-pressure circuit is by means of a centrifugal pump, in order to assure the required flow across the membranes. The liquid stream penetrating through the membrane is removed from the membrane module as permeate and collected in an argon-blanketed glass receiver. The permeate rate is detected continuously by means of a balance. The excess feed volume (retentate) is returned to the glass autoclave. This recycling is effected by means of a mechanical supply pressure regulator with which the supply pressure of the nanofiltration stage is also established. The circuit is heated by means of a thermostat, such that a defined temperature for the separation is assured.

The experiments were run under the following conditions: active membrane surface area 84.5 cm$^2$, transmembrane pressure 45 bar, separation temperature 25° C.

It is possible to take samples of the feed stream to the high-pressure circuit (feed), from the high-pressure circuit (retentate), and of the permeate. For analysis of the yield, 0.08 g of the sample and 0.03 g of ethylbenzene (internal standard) were weighed out and diluted with 0.25 g of acetonitrile. Further analysis was effected by means of GC-FID. The retention of ligands and metal was ascertained by means of ICP-OES after prior digestion of the samples of permeate and retentate. Analysis with regard to the retention of acid was effected by means of $^{19}$F NMR. Sample preparation and analysis for all three methods are known to the person skilled in the art.

The membrane material used was PEEK. The PEEK-acetone membrane according to the invention was produced in accordance with the publication J. da Silva Burgal et al.; Journal of Membrane Science, vol. 479 (2015), pp. 105-116 (see also WO 2015/110843 A1).

The contents of the glass autoclave were stirred in order to assure virtually ideal mixing. The pressure in the glass autoclave was adjusted to 10 bar by means of a mechanical supply pressure regulator. The glass autoclave is kept at the desired temperature by means of an oil bath with an external thermometer mounted in the glass autoclave.

First of all, the glass autoclave and the high-pressure circuit were filled with a base reaction mixture consisting of 56% by weight of MeOH, 40% by weight of DiB, 0.5% by weight of 1,2-bis((tert-butyl(pyridin-2-yl)phosphanyl)methyl)benzene (ligand), 3.4% by weight of aluminium triflate (acid) and 0.1% by weight of [Pd(acac)$_2$] (metal), inertized with argon at 10 bar and put into operation.

The glass autoclave was then heated up to internal temperature 100° C., and the initial argon flow was changed to CO (start of reaction). Over the course of 15 h, the base reaction mixture was pumped in circulation to start up the system. After 15 h, DiB in the feed had been converted to TMH ester to an extent of 99%. After 15 h, the circulation mode was ended, and the permeate was collected in separate glass vessels and fresh reaction solution (60% by weight of MeOH and 40% by weight of DiB) was metered in. No fresh catalyst, ligand or acid was added over the study duration of 105 h. For the respective study durations, the permeability, the yield of the TMH ester and the retentions for the components of the catalyst system were determined by the methods specified above.

TABLE 1

Continuous conversion of DiB to TMH ester

| Duration h | T(glass autoclave) ° C. | P kg/m$^2$h$^1$bar$^1$ | Y(TMH ester) * % | R(metal) % | R(ligand) % | R(acid) % |
|---|---|---|---|---|---|---|
| 0-15 | 100 | 0.045 | 99 | | ** | |
| 15-35 | 100 | 0.051 | 84 | 98 | 97 | 97 |
| 35-70 | 90 | 0.049 | 73 | 97 | 98 | 96 |
| 70-90 | 80 | 0.050 | 59 | 98 | 97 | 97 |
| 90-105 | 100 | 0.048 | 84 | 97 | 98 | 96 |

* Yield at the end of the experiment duration under consideration in each case
** No retentions ascertained (startup of the system)

It becomes clear from table 1 that, by virtue of the membrane separation, more than 97% of metal, ligand and acid is recycled. As a result, it is possible to achieve the same yield for the desired ester even without further addition of fresh catalyst system even over prolonged periods. Accordingly, the activity of the catalyst complex is not significantly affected by this method.

Example 2

Hydrogenation of the TMH Ester Obtained in Example 1 to TMH Alcohol

The collected permeate from Example 1 was separated by means of fractional distillation. First of all, methanol and unconverted diisobutene (DiB) were removed, before the methyl 3,5,5-trimethylhexanoate (TMH ester) was obtained. The TMH ester was then reacted in a 300 ml autoclave with a catalyst that comprised 15 w % Cu/1.8 w % Cr on a support (Stuttgarter Masse) at 200° C. and 270 bar H$_2$ for 20 h. After cooling and releasing the pressure, 1 ml of sample was taken, to which 150 µl of isooctane was added as internal standard, in order to determine the yield and n/iso selectivity by means of GC analysis. The yield was 98% TMH alcohol (n/iso: 99:1).

Example 3

Conversion of diisobutene (DiB) to methyl 3,5,5-trimethylhexanoate (TMH ester) with distillation as catalyst recycling The reaction was conducted as described in Example 1 (0.15 l of base reaction mixture consisted of 56% by weight of MeOH, 40% by weight of DiB, 0.5% by weight of 1,2-bis((tert-butyl(pyridin-2-yl)phosphanyl)methyl)benzene (ligand), 3.4% by weight of aluminium triflate (acid) and 0.1% by weight of [Pd(acac)$_2$] (metal)).

After commencement of the reaction, samples were taken hourly for 4 hours. For analysis of the yield, 0.08 g of the sample and 0.03 g of ethylbenzene (internal standard) were weighed out and diluted with 0.25 g of acetonitrile. Analysis was effected by the methods specified in Example 1. After 4 h, the reaction was ended and the reaction mixture was cooled down and the reactor was decompressed.

By applying vacuum (0.02 bar), the reaction solution was reduced to 0.02 l, and primarily methanol, unconverted DiB and TMH ester were collected via condensation, while the catalyst system remained in the glass autoclave. Analysis of a sample of the reaction mixture remaining in the reactor by means of GC-FID showed only traces of methanol and unconverted DiB (<2% by weight).

Subsequently, the glass autoclave was filled back to 0.15 l in order to perform a second run with a base reaction mixture composed of 60% by weight of MeOH and 40% by weight of DiB, and a further reaction was performed.

After commencement of the reaction, samples were taken hourly for 4 hours. For analysis of the yield, 0.08 g of the sample and 0.03 g of ethylbenzene (internal standard) were weighed out and diluted with 0.25 g of acetonitrile. Analysis was effected by the methods specified in Example 1. After 4 h, the reaction was ended and the reaction mixture was cooled down and the reactor was decompressed.

TABLE 2

Comparison of the conversion of DiB to TMH ester after employment of distillation

| Time of sampling h | Y(TMH ester) first run % | Y(TMH ester) second run % |
|---|---|---|
| 1 | 67 | 11 |
| 2 | 83 | 19 |
| 3 | 88 | 25 |
| 4 | 93 | 27 |

It becomes clear from Table 2 that distillation for removal of the reactants and products from the catalyst distinctly reduces the reactivity of the catalyst in the second run.

Example 4

The preparation was analogous to Example 1, except that di-n-butene (DnB) was used.

The collected permeate from Example 1 was separated by means of fractional distillation. First of all, methanol and unconverted di-n-butene (DnB) were removed, before the resultant ester methyl isononanoate was obtained. The ester obtained was then reacted in a 300 ml Paar autoclave with a 15 w % Cu/1.8 w % Cr catalyst supported on Stuttgarter Masse at 200° C. (closed-loop control based on internal temperature) and 270 bar H2 at 500 rpm for 20 h. After cooling and releasing the pressure, 1 ml of sample was taken, to which 150 µl of isooctane was added as internal standard, in order to determine the yield and n/iso selectivity by means of GC analysis (yield: 94% isononyl alcohol, (n/iso: 69:31)).

The invention claimed is:

1. A process for preparing a target alcohol, wherein the process comprises the following steps:
  a) preparing an ester by carbonylating a C2 to C16 alkene or isoalkene with carbon monoxide and with an alcohol A, which is a mono- or polyalcohol (two or more OH groups) having from 1 to 50 carbon atoms or is a mixture of two or more mono- and/or poly alcohols and which is used in a molar ratio to the C2 to C16 alkene or isoalkene (alcohol:C2 to C16 alkene or isoalkene) of from 2 to 20, in the presence of a homogeneous catalyst system comprising at least one metal of groups 8 to 10 of the Periodic Table of the Elements or a compound thereof, a phosphorus-containing ligand and an acid, in a reaction zone to obtain a liquid product mixture, wherein the carbon monoxide is directly supplied or by a carbon monoxide-containing gas selected from the group consisting of synthesis gas, water gas, and generator gas;
  b) performing a membrane separation to separate the homogeneous catalyst system from the liquid product mixture, which enriches the homogeneous catalyst system and additionally unconverted hydrocarbon and/or unconverted alcohol A in the retentate and enriches the ester formed in step a) in the permeate, wherein the membrane material used is an organic solvent nanofiltration membrane material which is acid-stable, stable in the presence of the acid of the catalyst system for at least 300 h, and which has at least one separation-active layer, and wherein the retentate is returned to the reaction zone in step a) and the permeate is routed to the subsequent step c);
  c) separating the ester formed in step a) from the permeate in at least one separation process step selected from the group consisting of thermal separation, distillation, extraction, crystallization and membrane separation;
  d) hydrogenating the ester separated in step c) with hydrogen in the presence of the heterogeneous catalyst system in a hydrogenation zone to obtain an alcohol mixture comprising at least the target alcohol, the eliminated alcohol A and unconverted esters; and
  e) separating the target alcohol formed in step d) in at least one separation process step selected from thermal separation, distillation, extraction, crystallization, and membrane separation.

2. The process according to claim 1, wherein the separation-active layer is composed of a PAEK polymer.

3. The process according to claim 2, wherein the separation-active layer is composed of PEEK having a degree of sulfonation of less than 20%.

4. The process according to claim 1, wherein the alcohol A used in step a) is a mono- or polyalcohol (two or more OH groups) having from 1 to 15 carbon atoms, or a mixture of two or more mono- and/or poly alcohols.

5. The process according to claim 4, wherein the alcohol A used in step a) is selected from the group consisting of methanol, ethanol, 1-propanol, 1-butanol, 1-pentanol, 1-hexanol, 2-propanol, tert-butanol, 3-pentanol, 2-propylheptanol, cyclohexanol, phenol and mixtures thereof.

6. The process according to claim 1, wherein the C2 to C16 hydrocarbon comprises at least one olefinic double bond.

7. The process according to claim 1, wherein the metal of groups 8 to 10 of the Periodic Table of the Elements or a compound thereof in the homogeneous catalyst system in step a) is palladium or a compound thereof.

8. The process according to claim 1, wherein the phosphorus-containing ligand in the homogeneous catalyst system has a bidentate structure.

9. The process according to claim 1, wherein the reaction in step a) is conducted at a pressure of from 5 to 60 bar.

10. The process according to claim 1, wherein the acid in the catalyst system in step a) is a Bronsted acid having a pKa≤5, or a Lewis acid having an LAU value of more than 25.

11. The process according to claim 1, wherein the acid in the catalyst system in step a) is a Bronsted acid or a Lewis acid, where the Bronsted acid is perchloric acid, sulfuric acid, phosphoric acid, methylphosphonic acid or a sulfonic acid, and where the Lewis acid is aluminium triflate, aluminium chloride, aluminium hydride, trimethylaluminium, tris(pentafluorophenyl)borane, boron trifluoride, boron trichloride or a mixture thereof.

12. The process according to claim 1, wherein the carbon monoxide-containing gas is the synthesis gas and is separated to obtain separated carbon monoxide and separated hydrogen upstream of the reaction zone and the carbon monoxide is routed to the reaction zone in step a) and the hydrogen separated to the hydrogenation zone in step d).

13. The process according to claim 2, wherein the separation-active layer is composed of PEEK.

14. The process according to claim 2, wherein the alcohol A used in step a) is a mono- or polyalcohol (two or more OH groups) having from 1 to 10 carbon atoms, or a mixture of two or more mono- and/or poly alcohols.

15. The process according to claim 1, wherein the acid in the catalyst system in step a) is a Bronsted acid having a pKa≤3, or a Lewis acid having an LAU value of more than 29.

16. The process according to claim 2, wherein the C2 to C16 hydrocarbon having at least one olefinic double bond which is used in step a) is an n- or isoalkene having from 2 to 16 carbon atoms.

* * * * *